US005754662A

United States Patent [19]

Jolly et al.

[11] Patent Number: 5,754,662

[45] Date of Patent: *May 19, 1998

[54] FREQUENCY-FOCUSED ACTUATORS FOR ACTIVE VIBRATIONAL ENERGY CONTROL SYSTEMS

[75] Inventors: Mark R. Jolly, Holly Springs; Mark A. Norris; Dino J. Rossetti, both of Raleigh; Douglas A. Swanson, Apex; Steve C. Southward, Cary, all of N.C.

[73] Assignee: Lord Corporation, Cary, N.C.

[ * ] Notice: The term of this patent shall not extend beyond the expiration date of Pat. No. 5,526,292.

[21] Appl. No.: 347,521

[22] Filed: Nov. 30, 1994

[51] Int. Cl.$^6$ ............................ H03B 29/00; A61F 11/06

[52] U.S. Cl. .................. 381/71.4; 381/71.11; 381/71.14

[58] Field of Search ........................................ 381/71, 94

[56] References Cited

U.S. PATENT DOCUMENTS

| | | | |
|---|---|---|---|
| 3,936,606 | 2/1976 | Wanke . | |
| 4,506,380 | 3/1985 | Matsui | 381/71 |
| 4,689,821 | 8/1987 | Sulikuddin et al. | 381/71 |
| 4,715,559 | 12/1987 | Fuller . | |
| 4,815,139 | 3/1989 | Eriksson et al. | 381/71 |
| 5,060,271 | 10/1991 | Geddes | 381/71 |
| 5,111,507 | 5/1992 | Nakaji | 381/71 |
| 5,131,047 | 7/1992 | Hashimoto et al. | 381/71 |
| 5,133,017 | 7/1992 | Cain et al. | 381/71 |
| 5,146,505 | 9/1992 | Pfaff et al. | 381/71 |
| 5,170,433 | 12/1992 | Elliott et al. | 381/71.9 |
| 5,216,722 | 6/1993 | Popovich | 381/71 |
| 5,229,556 | 7/1993 | Geddes . | |
| 5,245,552 | 9/1993 | Andersson et al. . | |
| 5,245,664 | 9/1993 | Kinoshite et al. | 381/71 |
| 5,251,262 | 10/1993 | Suzuki et al. | 381/71 |
| 5,267,320 | 11/1993 | Fukumizu | 381/71 |
| 5,267,321 | 11/1993 | Langberg | 381/72 |
| 5,272,286 | 12/1993 | Cain et al. . | |
| 5,316,240 | 5/1994 | Girard et al. . | |
| 5,526,292 | 6/1996 | Hodgson et al. | 381/71.4 |

FOREIGN PATENT DOCUMENTS

| | | |
|---|---|---|
| 0 457 176 A2 | 5/1991 | European Pat. Off. . |
| 0 560 364 A1 | 3/1993 | European Pat. Off. . |
| 2 257 327 | 6/1992 | United Kingdom . |

*Primary Examiner*—Curtis Kuntz
*Assistant Examiner*—Xu Mei
*Attorney, Agent, or Firm*—Randall S. Wayland; James W. Wright

[57] ABSTRACT

Actuators for active vibrational energy control systems which are frequency focused. The high-frequency cancellation function is decoupled from the low-frequency cancellation function to enable the size, force, number and placement of the actuators to be optimized. A hybrid system employing structural actuators to cancel low-frequency vibrations and speakers to cancel higher-frequency vibrations is also taught.

18 Claims, 11 Drawing Sheets

FREQUENCY-FOCUSED ACTUATORS FOR ACTIVE VIBRATIONAL ENERGY CONTROL SYSTEMS

BACKGROUND AND SUMMARY OF THE INVENTION

The present invention is directed to an active noise and vibration control (ANVC) system. More particularly, the present invention relates to certain improvements in ANVC systems permitting enhancement of control over a range of frequencies including broadband control and optimization of total energy within the system.

The present application is related to application Ser. No. 08/347,523, filed Nov. 30, 1994 entitled "Broadband Noise and Vibration Reduction".

Various active noise control (ANC) systems have been proposed which generate an inverted-phase signal of comparable frequency and magnitude to the input, or disturbance, signal which combines destructively with the disturbance signal to eliminate or, at least, significantly reduce the noise within a control volume such as, for example, the interior of an aircraft cabin. A broadband actuator, typically a speaker, has to be of significant size to produce the low-frequency vibrations (20–100 Hz) needed for destructive interference making their placement within the cabin problematic. The problem is aggravated by the fact that in order to control the high-frequency vibrations in the range of 100–500 Hz, there needs to be a large number of speakers because of the increased number of modes. Normally, for higher frequencies the control efficiency tends to be localized within one-tenth of a wavelength from the closest error sensor (which is generally a microphone). The placement of actuators is more critical for high-frequency vibrations.

Similar problems arise in active vibration control (AVC) systems with actuators having to be sized to accommodate the low-frequency (typically, high amplitude) vibrations while the number utilized must be determined by the highest frequency for which control is desired. In addition, systems like Fuller (U.S. Pat. No. 4,715,559) which solely employ actuators to control sound energy to cancel tonal noise can actually input large amounts of vibrational energy into the system to accomplish optimum sound reduction at the error microphones. This increased vibrational energy put into the system can have a negative impact on the fatigue life of the structure. Further, optimum passenger comfort is actually arrived at by a compromise solution resulting in a less-than-optimum noise control in favor of avoiding excessive structural vibration.

The present invention solves the problems of the prior art ANVC devices by subdividing the control responsibility of the low (20–100 Hz, for example) frequency from the high-frequency (100–500 Hz) actuators by frequency focusing the respective actuator groups, permitting the physical size, the force capability, and the number of actuators in the respective groups to be optimized for the application. The term "actuator" when used herein shall include both speakers and structural actuators such as inertial shakers and piezoelectric actuators unless otherwise specified. Further, although the term "high-frequency" is used here to contrast it from the low-frequency band described herein, the range of 100–500 Hz is normally regarded as midrange. Finally, the term "vibrational energy" when used herein shall refer to both structural vibrational and audible or sound vibrational energy.

Another aspect of the present invention is a hybrid speaker and structural actuator system which employs these actuators to maximize the respective advantages of each. Elliott et al. (U.S. Pat. No. 5,170,433) infers a system which uses a combination of equal numbers of speakers and inertial actuators to cancel one or more harmonics of a tonal noise signal (FIG. 10). The present invention uses structural actuators to control noise in the low-frequency range (≦70 Hz) where the interior noise is directly coupled to the structural vibration. Either microphones or accelerometers could serve as error sensors for the low-frequency actuators. In the high-frequency range where the interior noise is not directly coupled to structural vibration, it is preferred to use speakers to control noise so as not to increase the structural vibrational energy in the compartment while quieting the noise. Microphones should be used as error sensors in the high-frequency range. While microphones may be shared as error sensors for both low- and high-frequency actuators, the accelerometers should be frequency focused for use by only the structural actuators.

It is well known that the number of actuators required for a particular ANVC system is equal to the number of vibrational energy modes participating in the system response. If a particular cabin is, through experimentation, shown to have K vibrational energy modes, then the number of low-frequency actuators M needed to achieve global noise reduction is given by the expression $M \geqq K$. For high-frequency control, where the number of vibrational energy modes is greater, it is generally impractical to achieve global control due to the large number of actuators needed. For local control, which produces optimum control efficiency within one-tenth of a wavelength of the error sensor, the number of actuators N needed is related to the number of sensors L by the expression $N \geqq L/2$; that is, the number of actuators must be equal to or greater than one half the number of error sensors employed in the system to produce the desired reduction of sound at each of the error sensors.

The majority of ANC and ANVC systems have tonal-control capability only, that is, they are not able to handle multiple tones and/or background noise. The present invention includes, as one aspect thereof, an ANVC system employing a broadband reference-signal-detecting means producing an output signal indicative of the broadband noise and vibration to be canceled within the cabin, error sensor means for detecting a residual level of vibrational energy within the cabin downstream of said reference signal means, actuator means capable of generating a phase-inverted signal to reduce at least some portions of the broadband vibrational energy within said compartment, and a broadband controller which includes a plurality of adaptive filters for generating broadband, time-domain command signals which activate said actuators to produce the desired control signal(s).

Various other features, advantages and characteristics of the present invention will become apparent after a reading of the following detailed description thereof.

BRIEF DESCRIPTION OF THE DRAWINGS

The figures set forth the preferred embodiments in which like reference numerals depict like parts.

DETAILED DESCRIPTION OF THE PREFERRED EMBODIMENTS

Figure 1:
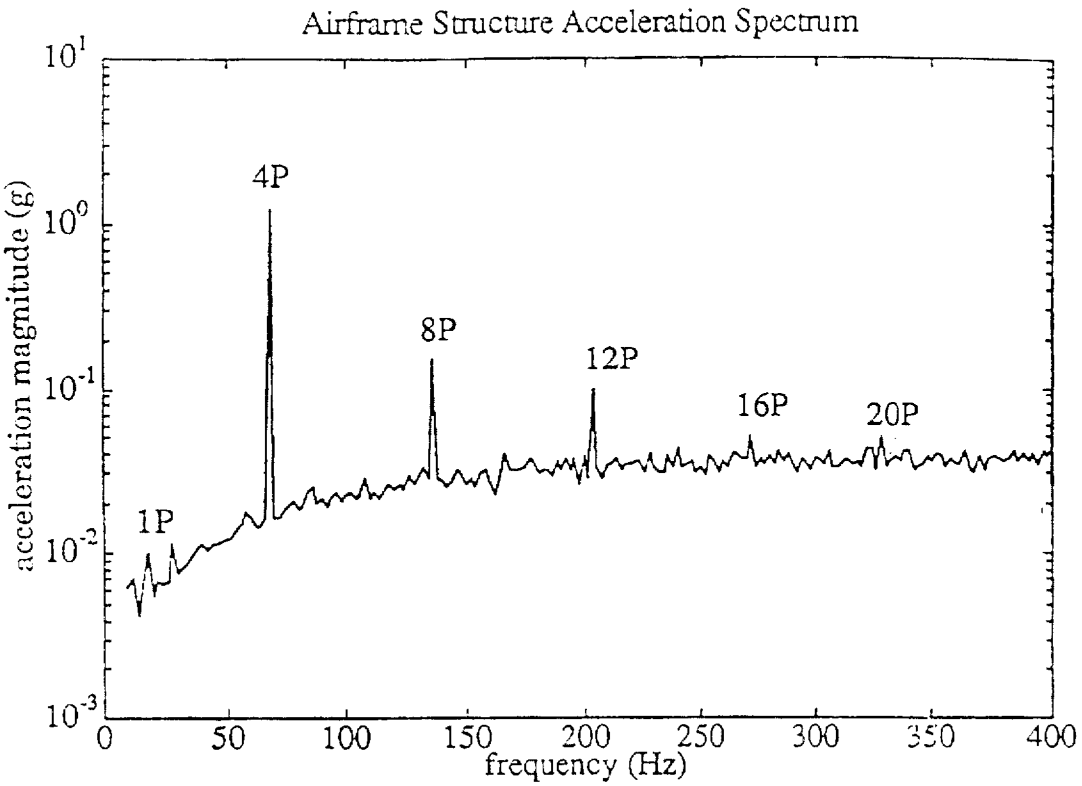
FIG. 1 is an acceleration vs. frequency plot for a typical turboprop airframe.

One of the features of the present invention is frequency-focused actuation, that is, that individual actuators can be designed to operate predominantly in a specific frequency range, the presumption being that multiple ranges are beneficial. For example, in a turboprop aircraft application, different actuators could be used to control interior noise and structural vibration at the 4P, 8P, 12P, etc., blade passage frequencies. If P is the rate of rotation of the drive shaft of an engine in revolutions per second, then 4P will be the passage frequency of a four-bladed prop, 8P the first harmonic, 12P the second harmonic, etc. Typically, for turboprop applications, the blade pass frequency and its harmonics tend to be the principal contributors to the cabin vibration, and its resultant interior noise, as shown in FIG. 1.

The principle involved in frequency-focused actuators is that for a particular enclosure, a small number of actuators are needed to globally control vibrational energy at low frequencies because both acoustic and structural modal density is relatively small. At high frequencies, a larger number of actuators is needed to control both noise and vibrational energy because modal density increases. Because the force requirements are generally different for the different frequency ranges, because the placement of large actuators is difficult, and because the placement of the high-frequency actuators is critical, it makes sense to subdivide the low- and high-frequency actuators to attack these different frequency ranges of an input signal having different spectral frequencies.

For applications where use of speakers is appropriate, a first group of low-frequency speakers or sub-woofers is used. The number M in this group will ordinarily be equal to or greater than the number K of dominant low-frequency modes within the passenger compartment; that is, $M \geqq K$. The number of speakers in the group of midrange or higher-frequency speakers will typically need to be greater since modal density is higher and control is localized around the error microphones. It is preferred that the number N of high-frequency speakers be equal to or greater than one-half the number of error microphones L; that is $N \geqq L/2$. By subdividing the lowand high-frequency responsibilities, the low-frequency speakers can be adequately sized to perform their function and the high-frequency speakers can be adequately numbered and positioned to more efficiently perform their function. The frequency-focusing concept allows the configuration of the cabin and what we know about its acoustic behavior to be used advantageously to enhance performance of the ANVC system.

Figure 2:
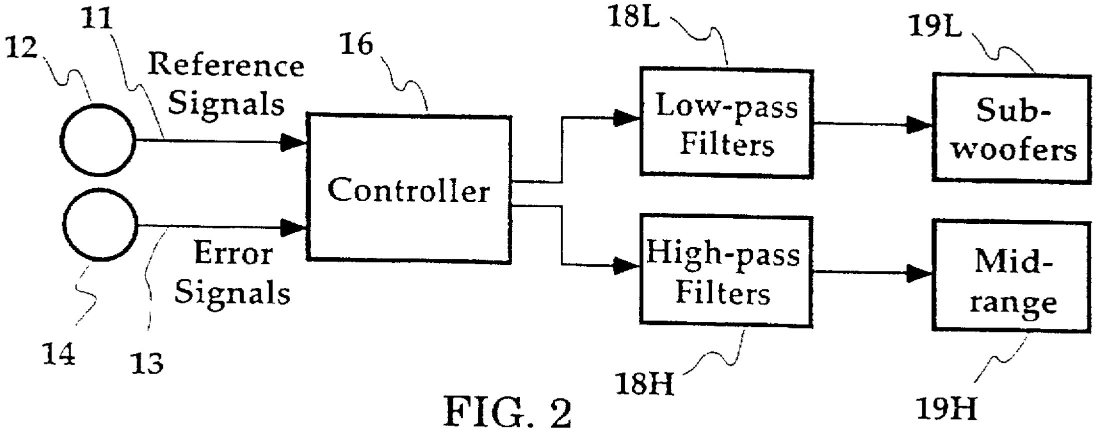
FIG. 2 is block diagram of a first control system to implement frequency focusing.

Frequency focusing can be implemented in at least four ways. A first way is depicted in FIG. 2 where reference signals 11 are fed from a reference sensors 12 and error signals 13 are fed from sensors 14 through controller 16 to filters 18L and 18H which exclude frequencies outside the band so the signal which is fed to the respective low frequency speaker 19L or high-frequency speaker 19H (identified here as midrange) is in the desired range. When this system is initialized, system ID will result in each of the band-pass filters being assigned a very small transfer function for frequencies outside the respective filter's band. This, in essence, imposes a cross-over frequency on the system.

Figure 3:
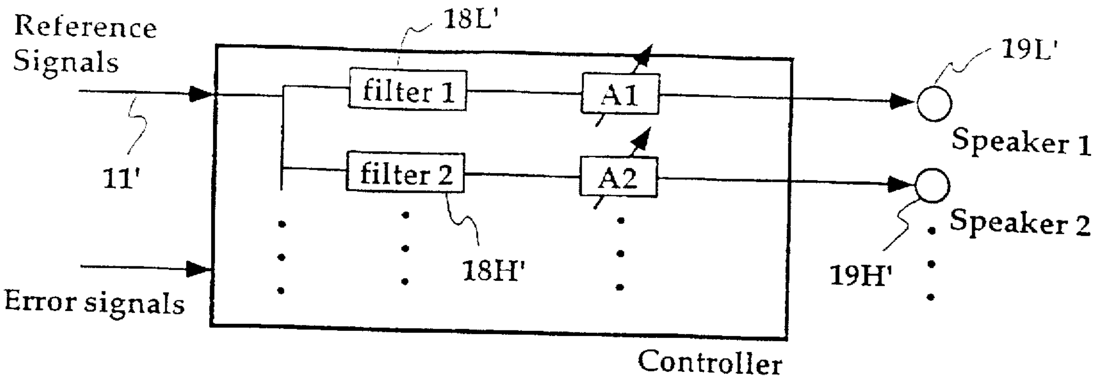
FIG. 3 is a block diagram of a second control system for implementing frequency focusing.

A second way to frequency-band focus the speakers is depicted in FIG. 3. In this embodiment, band-pass filters 18L' and 18H' are internalized within the controller and the reference signals 11' are subdivided for the respective speakers 19L' and 19H' and these reference signals are filtered after being split.

Yet a third way for frequency-band focusing the speakers is to utilize separate controllers in parallel, one controlling the low-frequency speakers and one controlling the high-frequency speakers. The controllers may use dedicated or shared error sensors.

Figure 4A:
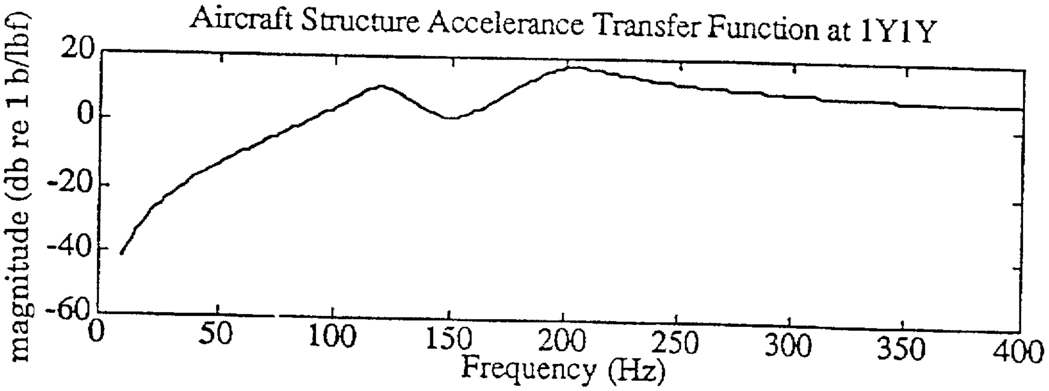
FIG. 4*a* is magnitude vs. frequency plot for an aircraft structure accelerance transfer function at 1Y1Y.
Figure 4B:
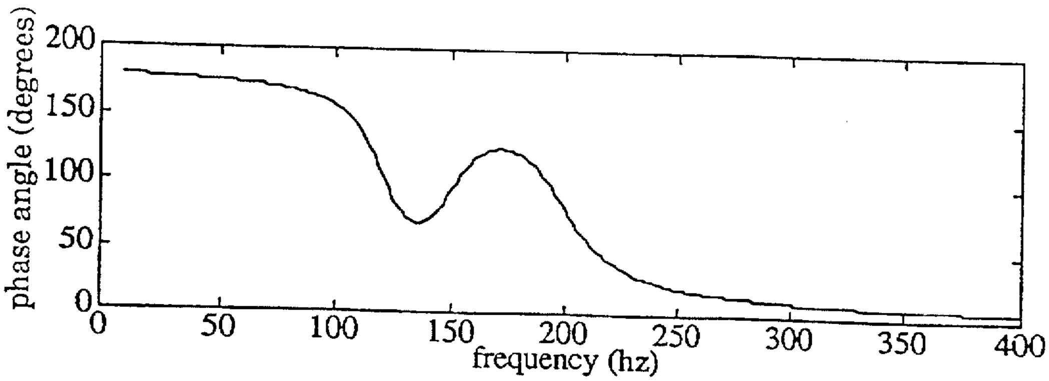
FIG. 4*b* is the phase angle vs. frequency plot of the transfer function shown in FIG. 4*a*.
Figure 5:
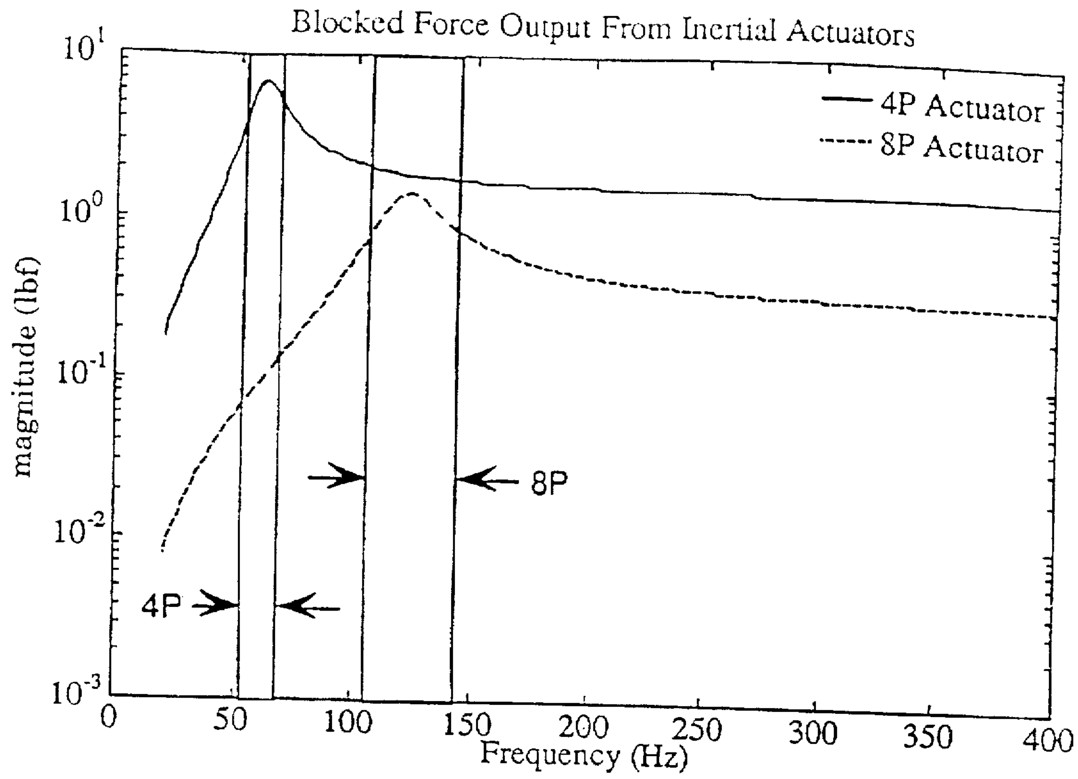
FIG. 5 is a magnitude vs. frequency plot for typical force output from inertial actuators.

Similar techniques can be used in frequency focusing structural actuators, as well. FIG. 4*a* shows the magnitude of the structural accelerance transfer function of a typical turboprop fuselage. FIG. 4*b* shows a typical phase angle vs frequency plot for the same structure. From the plot shown in FIG. 1 (which is taken from the same turboprop fuselage) and the plots of FIGS. 4*a* and 4*b*, it can be demonstrated that an inertial actuator capable of controlling the 4P peak would need to have a force output of five pounds while the force needed to handle the 8P peak would need only be sized to produce 0.2 pounds. The efficiencies gained from subdividing the cancellation functions of the 4P and 8P tones will be readily apparent. The inertial actuators in each case should be tuned for the lower end of their respective frequency ranges in order to provide adequate control force. The weight reduction for required actuators is also significant. The blocked force required for each of the inertial actuators is shown in FIG. 5.

Figure 6:
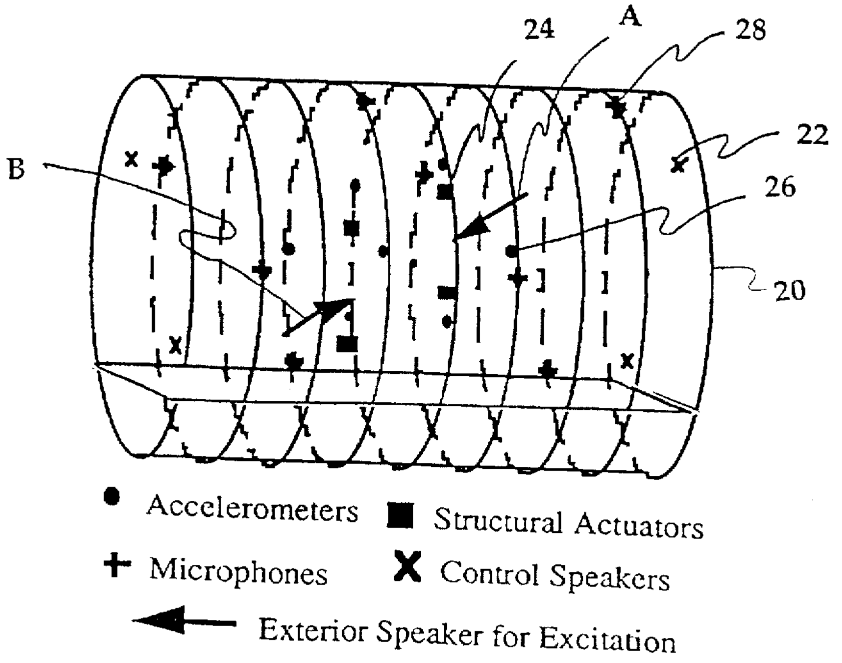
FIG. 6 is a schematic representation depicting the relative locations of accelerometers, actuators, microphones and control speakers within an aircraft cabin.

A series of tests were conducted using an existing aircraft cabin or fuselage 20 as seen in FIG. 6. The interior of cabin 20 was equipped with a series of speakers 22 and structural actuators 24 as counter-vibration producing elements and accelerometers 26 and sixteen microphones 28 as feedback or error signal sensors. Two external speakers were mounted on the exterior of the fuselage at A and B to simulate engine noise impinging on the cabin 20. Recorded engine noise was fed to the external speakers and the various ANVC elements employed to reduce the internal cabin noise.

Figure 7A:
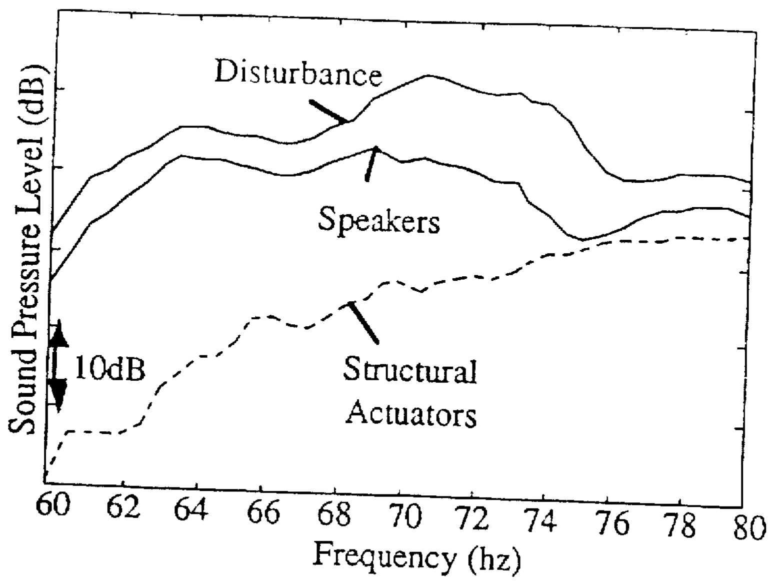
FIG. 7*a* is a plot of sound pressure vs. frequency in the low-frequency range for the control system depicted in FIG. 6.

FIG. 7a illustrates the average sound pressure level inside the fuselage over the 4P frequency range for both structural based actuators and speakers. Microphones were used as the error sensors. It is noteworthy that the structural based actuators achieve greater noise reductions below about 75 Hz.

Figure 7B:
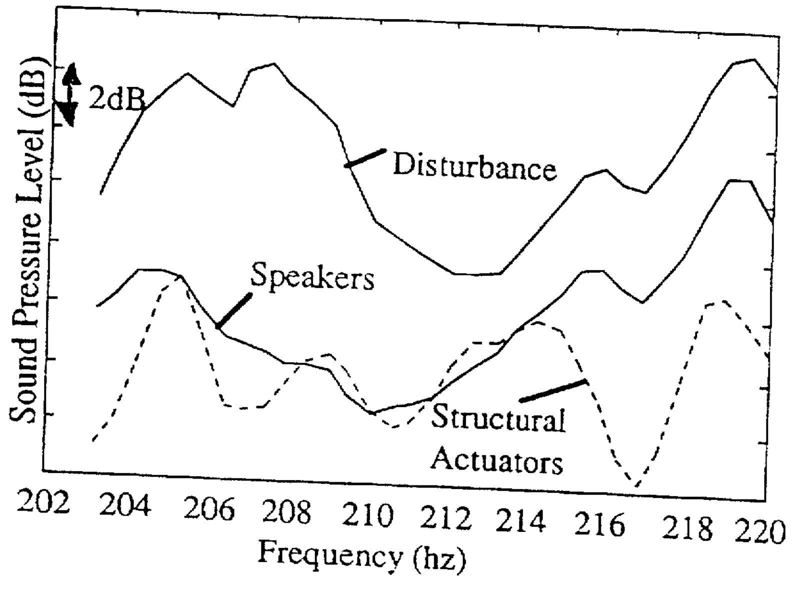
FIG. 7*b* is a plot of sound pressure vs. frequency in the higher-frequency range for the control system depicted in FIG. 6.

FIG. 7b illustrates the average sound pressure level inside the fuselage over the 12P frequency range for both structural based actuators and speakers. Again, microphones were used as the error sensors.

FIGS. 7a and 7b demonstrate that structural based actuators can achieve greater noise reductions than speakers over the 4P frequency range. They also show that the noise reductions achieved using structural based actuators and speakers are comparable over the 12P frequency range. If noise alone were the criteria for choosing actuators, then structural based actuators would probably be used to reduce interior noise at the 4P frequency range and structural based actuators or speakers could be used to reduce noise over the 12P frequency range.

Figure 8A:
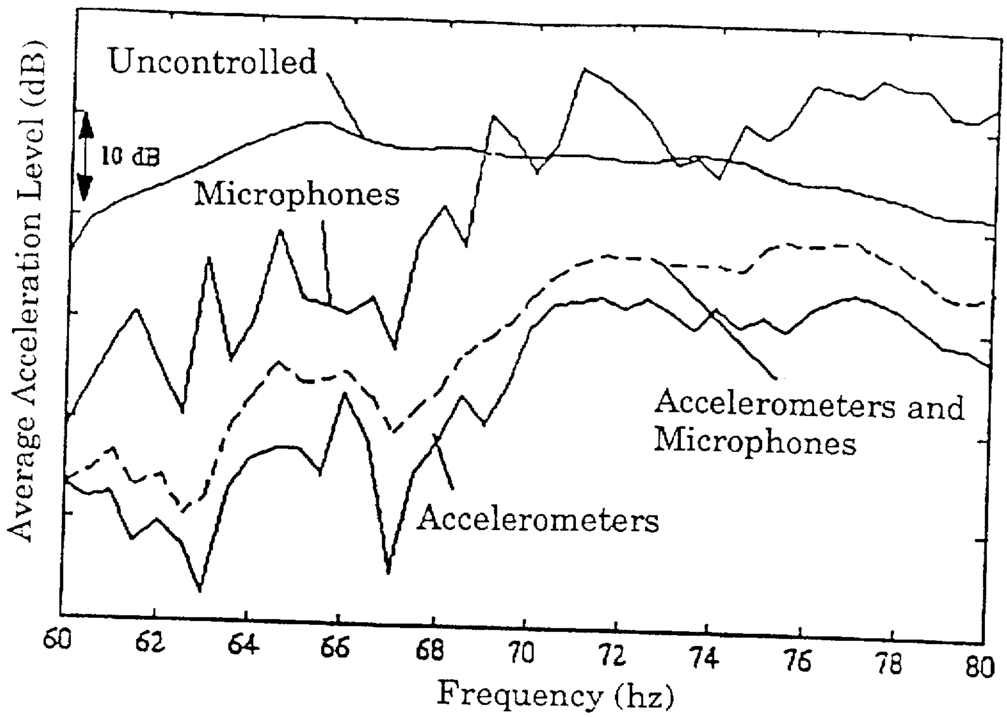
FIG. 8*a* is a plot of average acceleration vs. frequency using structural based actuators with various control sensors over the 4P range.

FIG. 8a shows the average fuselage acceleration over the 4P frequency range for structural based actuators using accelerometers, microphones, and combinations thereof. Note that because speakers do not affect structural vibration, the uncontrolled vibration level shown in FIG. 8a is equivalent to the controlled vibration level when speakers and microphones are used. FIG. 8a illustrates that structural based actuators can achieve significant vibration reductions. Below 70 Hz, either microphones or accelerometers could be used as the error sensors. Above 70 Hz, however, a combination of accelerometers and microphones should be used to ensure that both vibration and noise is reduced. In the 4P frequency range, the structural based actuator control system significantly outperforms a speaker based control system.

Figure 8B:
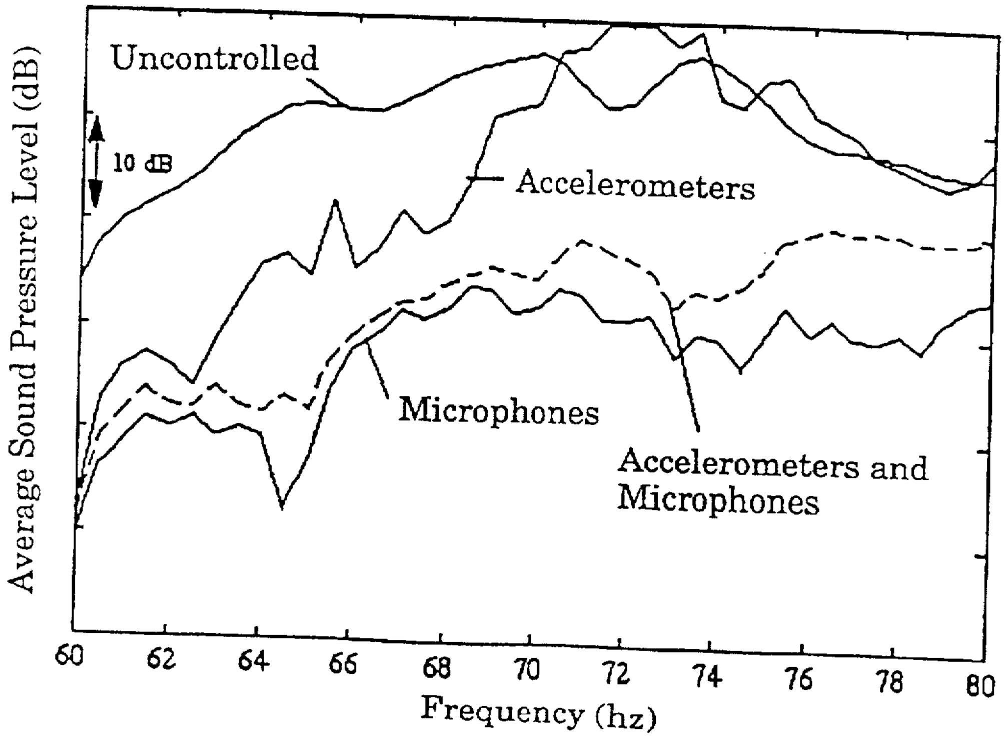
FIG. 8*b* is a plot of average sound pressure level vs. frequency using structural based actuators with various control sensors over the 4P range.

FIG. 8b shows the average sound pressure level over the 4P frequency range for structural based actuators using accelerometers, microphones, and combinations thereof. It can be seen that a control system with structural based actuators and microphones and accelerometers as error sensors provided excellent reductions in both sound pressure level and structural vibration. Over the 4P frequency range, the structural vibration is directly coupled to the acoustics, resulting in significant vibration and noise reductions. Over this frequency range, structural based actuators should be used with microphones and/or accelerometers.

Figure 9A:
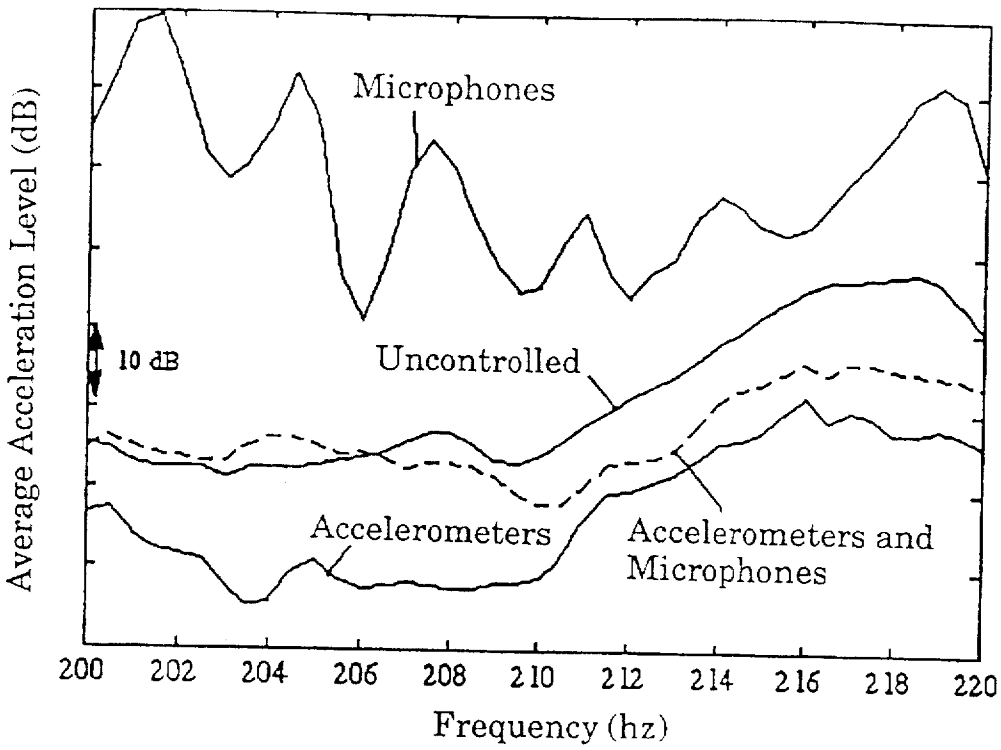
FIG. 9*a* is a plot of average acceleration vs. frequency using structural based actuators with various control sensors over the 12P range.
Figure 9B:
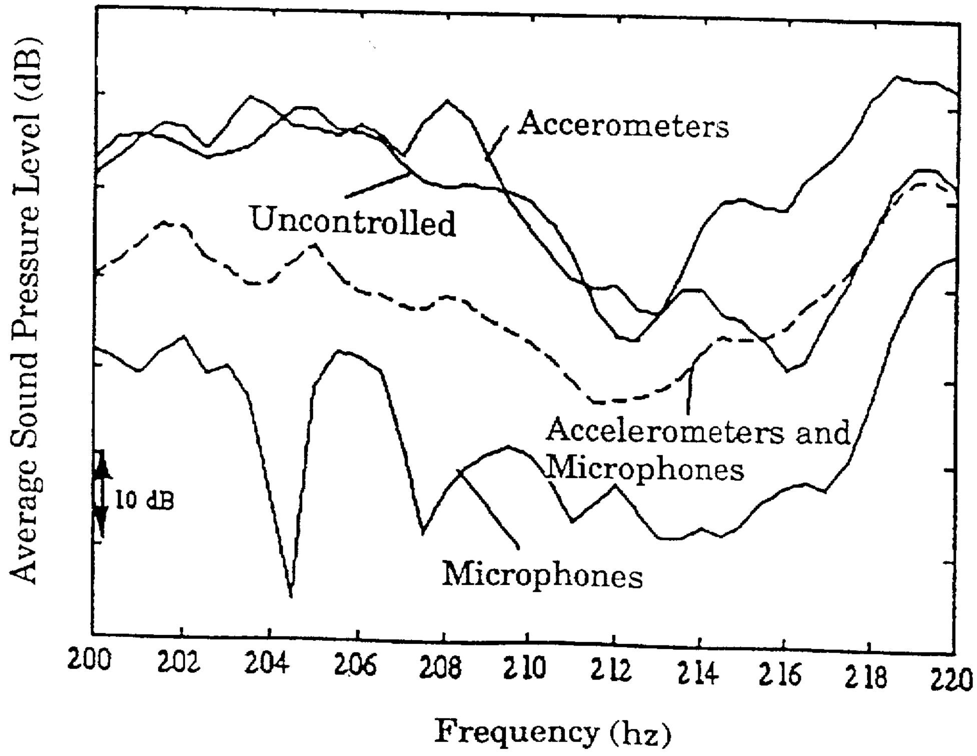
FIG. 9*b* is a plot of average sound pressure level vs. frequency using structural based actuators with various control sensors over the 12P range.

FIGS. 9a and 9b illustrate the average fuselage acceleration and sound pressure level over the 12P frequency range for structural based actuators using accelerometers, microphones, and combinations thereof. Again, note that because speakers do not affect structural vibration, the uncontrolled vibration level shown in FIG. 9b is equivalent to the controlled vibration level when speakers and microphones are used. These two figures show that the structural vibration is not directly coupled to the noise in the 12P frequency range. A structural based actuator can significantly increase structural vibration when controlling interior noise. In this frequency range, speakers should be used with microphone error sensors to reduce noise only. The structural vibration will remain unchanged.

Figure 10:
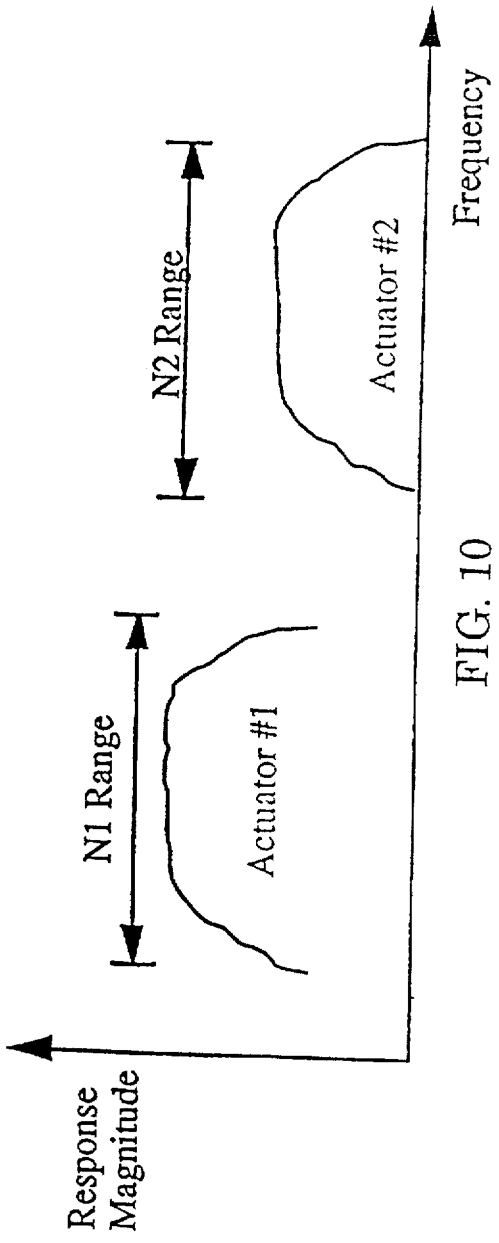
FIG. 10 is a plot of actuator response magnitude vs. frequency.

The use of frequency focused actuators requires the implementation of a modified control algorithm. Without loss of generality, the algorithm will be described with reference to two frequency ranges (an "N1" range and an "N2" range). The results discussed here are, however, directly generalizable to include more than two frequency ranges. For convenience, let actuator #1 be appropriately designed to handle the N1 frequency range and actuator #2 be appropriately designed to handle the N2 frequency range. Note that the response magnitudes of the different actuators do not have to be equal. This is described graphically in FIG. 10. It is noted that each algorithm has a software or math component and a hardware component. This discussion focuses on the differences in the hardware component.

Figure 11:
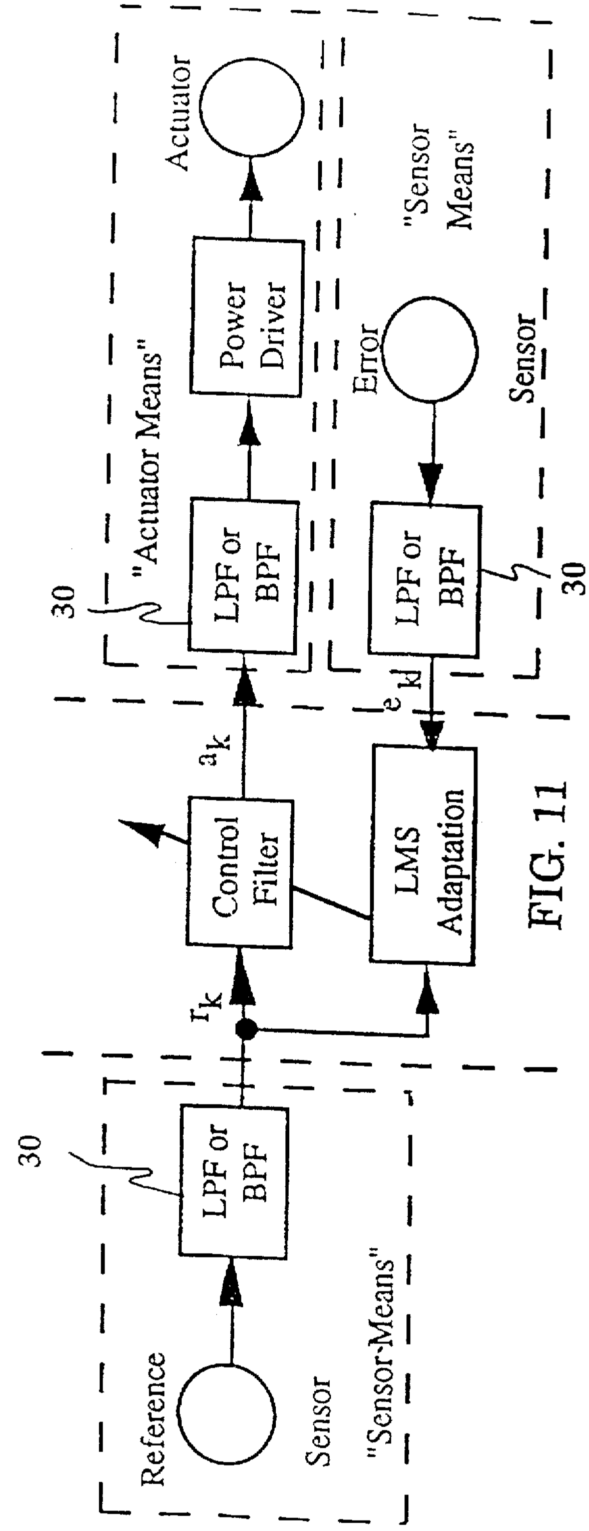
FIG. 11 is a block diagram for a SISO cancellation algorithm.

FIG. 11 is a block diagram of a single input-single output LMS cancellation algorithm embodying the principles of the invention. This algorithm will be implemented in multiple controllers with a first one tuned to a first frequency range and the second to another frequency range. Low pass filters (LPF) or, alternatively, band pass filters (BPF), 30 may be used. While filters 30 have been depicted as analog filters, they could be implemented digitally as well. For every actuator, there is a corresponding power driver and filter which together make up what can be called the actuator means. For every sensor there is a corresponding filter which together make up what is called the "sensor means". The term $r_k$ is defined to be the reference sensor samples, $a_k$ to be the actuator command samples, and $e_k$ to be the error sensor samples. A basic property of the LMS algorithm is that the control filter is made to converge to a filter which tends to reduce/eliminate any spectral components in $e_k$ which are directly correlated with the spectral components in $r_k$. Using frequency-focused actuators with the existing algorithms could potentially cause the control filters to respond to out-of-range spectral energy by continually increasing the output spectral components out of this range. This would inevitably lead to saturation at either the power driver, analog filter, or most likely the digital output device (e.g. D/A converter). In any event, overall performance would very likely be degraded without the practice of this invention.

Figure 12:
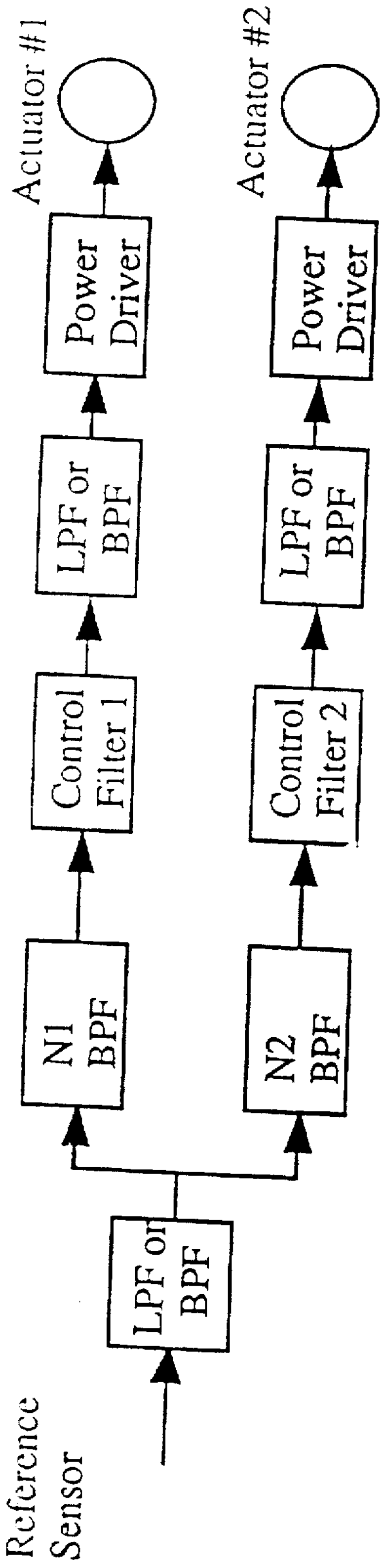
FIG. 12 is block diagram for a frequency focused controller.

For any frequency focused actuator, at least the corresponding reference sensor means must also be frequency focused, as well. In order to improve the convergence of the control filter, the error sensor means could also be frequency focused, although for most applications this is not necessary, and would unnecessarily increase the implementation cost. For example, microphone error sensors do not have to be frequency focused. They can be shared by both speakers and structural based actuators. Accelerometers, however, have to be frequency focused so that they are used only by structural based actuators and not speakers. For the two frequency focused actuators and a single reference sensor, this invention would take the form shown in FIG. 12 (without describing the LMS adaptation paths).

In some rare cases, we may have an application where individual reference sensors can be found which are already frequency focused. The simplest example is a filtered tachometer signal. In this case, the implementation would obviously follow from the preceding discussion. Another extension of this idea is to use sync or tach signals to locate the center frequency of an adjustable band pass filter.

According to the results of these tests, actuators and sensors should be chosen as follows:

(1) Use structural based actuators (i.e., inertial force actuators, active vibration absorbers or shaped PZT strips) to reduce both vibration and noise in frequency ranges where the interior noise is directly coupled to the structural vibration. Generally, this occurs at "low" frequencies, where there are few acoustic modes. Accelerometers and/or microphones could be used as the error sensors for this frequency range. Structural actuators should be used in this frequency range because interior noise and structural vibration can be reduced simultaneously. If speakers were used as actuators, then the interior noise would be reduced but the structural vibration would not. Structural based actuators should also outperform speakers in reducing interior noise in these frequency ranges.

(2) Use acoustic based actuators (i.e., speakers—woofers, mid-range, tweeters) to reduce noise only in frequency ranges where the interior noise is not directly coupled to the structural vibration. Generally, this occurs at "high" frequencies, where there are many acoustic modes. Microphones only should be used as the error sensors in this frequency range. Speakers should be used in this frequency range because they will greatly reduce interior noise without affecting structural vibration. Structural based actuators should not be used in these frequency bands because structural based actuators can increase structural vibration when reducing noise.

For an active control system that consists of both structural based actuators and speakers, microphones can be shared as the error sensors. Accelerometers, however, should be frequency focused so that they are only used in frequency ranges where structural based actuators are used. For maximum efficiency, the actuator resonances should be tuned to the low end of the desired frequency range.

Figure 13:
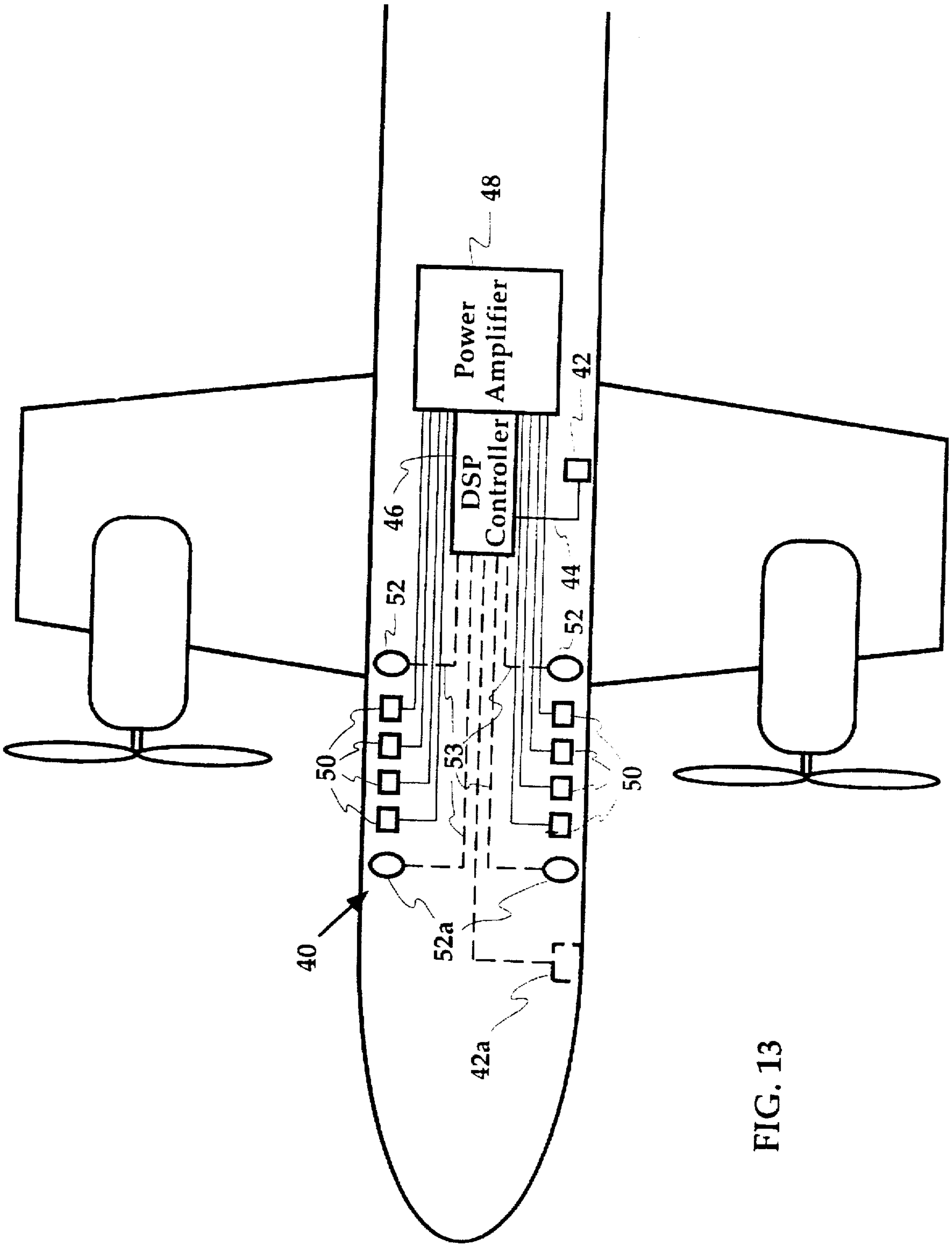
FIG. 13 is a schematic top view of a broadband control system in a turboprop application.
Figure 14:
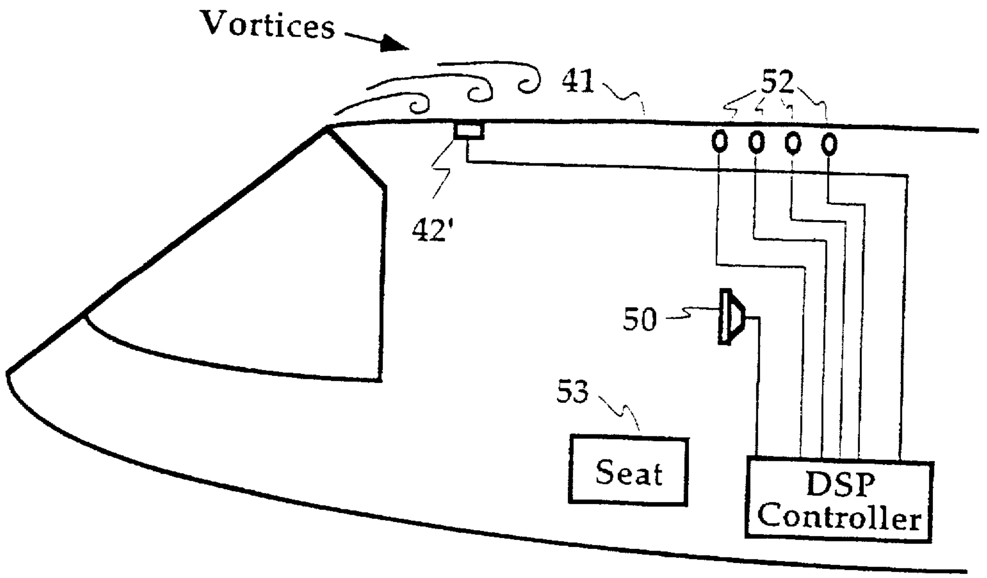
FIG. 14 is a schematic side view of a broadband control system in a slightly varied turboprop or turbofan application.
Figure 15:
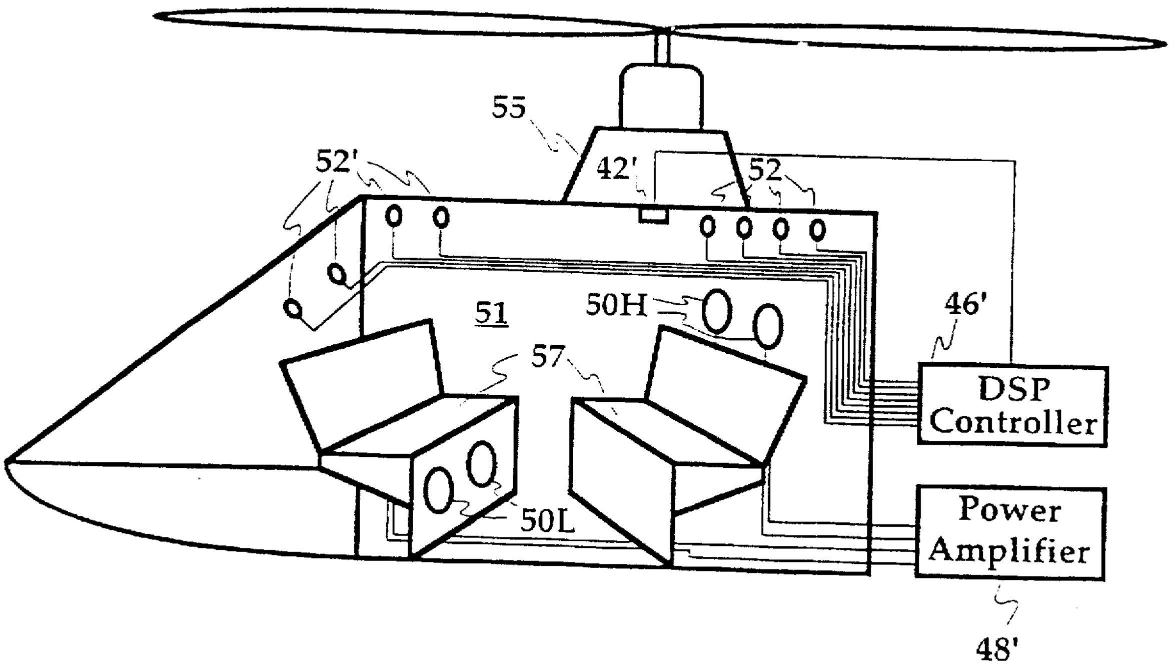
FIG. 15 is a schematic side view of a broadband control system in a rotary wing application.

Another feature of the present invention is the provision of an active noise and vibration system capable of broadband control. Several embodiments of the system 40 are depicted in FIGS. 13–15. FIG. 13 shows the broadband control system 40 employed in a turboprop aircraft 41. The broadband control system 40 includes reference sensor 42, which may be a microphone or accelerometer, to sense the frequency spectrum and corresponding relative magnitude of a broadband disturbance signal. A critical aspect of this inventive feature is the positioning of this sensor 42 in a key location with respect to the broadband disturbance source. In the FIG. 13 embodiment, sensor 42 is shown as being positioned on a wing spar near a portion of the fuselage 41 which is subject to prop wash. A similar key location might be near a door or window opening where boundary layer and/or engine noise might be significantly increased. The broadband signal 44 is fed to a digital signal process (DSP) controller 46 which generates a series of command signals which are fed through power amplifier 48 to a bank of actuators 50. The actuators may be speakers or structural actuators including inertial shakers or PZT strips, or a combination of speakers and structural actuators in which case, cancellation can occur in accordance with the frequency focused technique described above. Error sensors 52 which are preferably microphones provide the error signals 45 which are fed back to the controller to tweak the command signals to improve the overall sound and vibration control.

Sensor 42a shown in an alternative dotted line position in FIG. 13 is positioned in the nose of the aircraft to pickup the broadband input signal of the external air noise such as created by the vortices in the boundary layer (see FIG. 14). Error sensors 52 are shown inside the cabin proximate the top of fuselage 41 although alternative positions are possible. For example, both the error sensors 52 and the speakers 50 may be mounted in the head rest of the seats 53 to provide a zone of silence in the vicinity of the passenger's ears.

Figure 16:
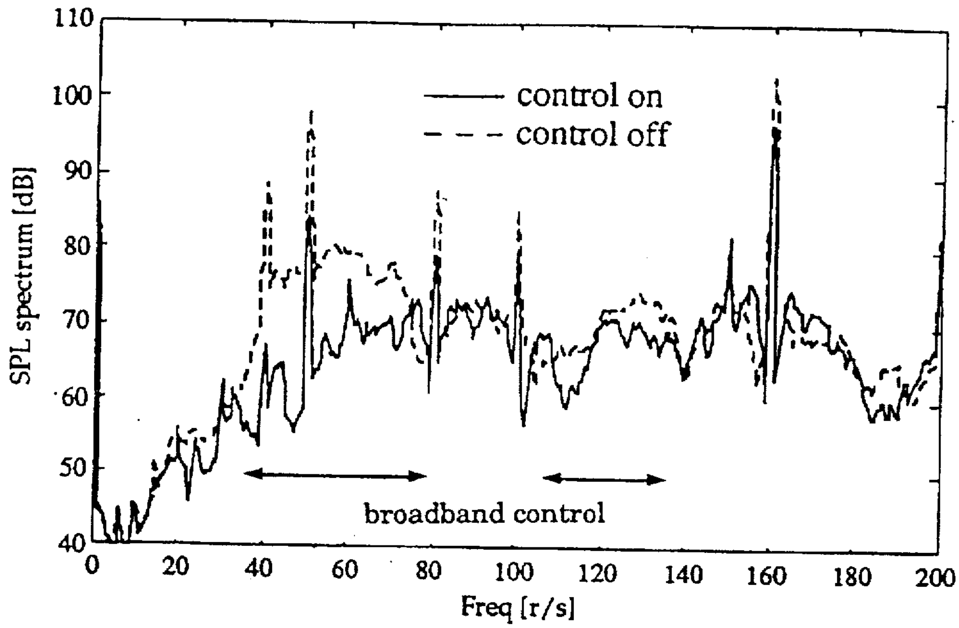
FIG. 16 is plot of sound pressure level vs. frequency for a broadband control system in a configuration similar to that shown in FIG. 15.

Another embodiment of broadband control system 40' is shown in a helicopter cabin (FIG. 15). In this case, reference sensor 42' is positioned within the cabin adjacent the ceiling to pickup the vibrational energy transmitted by gear box 55. The command signals are fed by the controller 46' through amplifier 48' (which could be built into the controller) to actuators/speakers 50L and 50H, the low-frequency actuators 50L being positioned beneath the seats 57 and the high frequency speakers 50H are mounted on the headrests of seats 57. Error sensors 52' are shown distributed about the upper portion of the cabin walls to provide zones of control proximate the passengers' ears. A configuration much like that depicted in FIG. 15 was used to generate the data shown in FIG. 16. The residual spikes shown there could be further reduced by application of the frequency focusing principles discussed herein.

Figure 17:
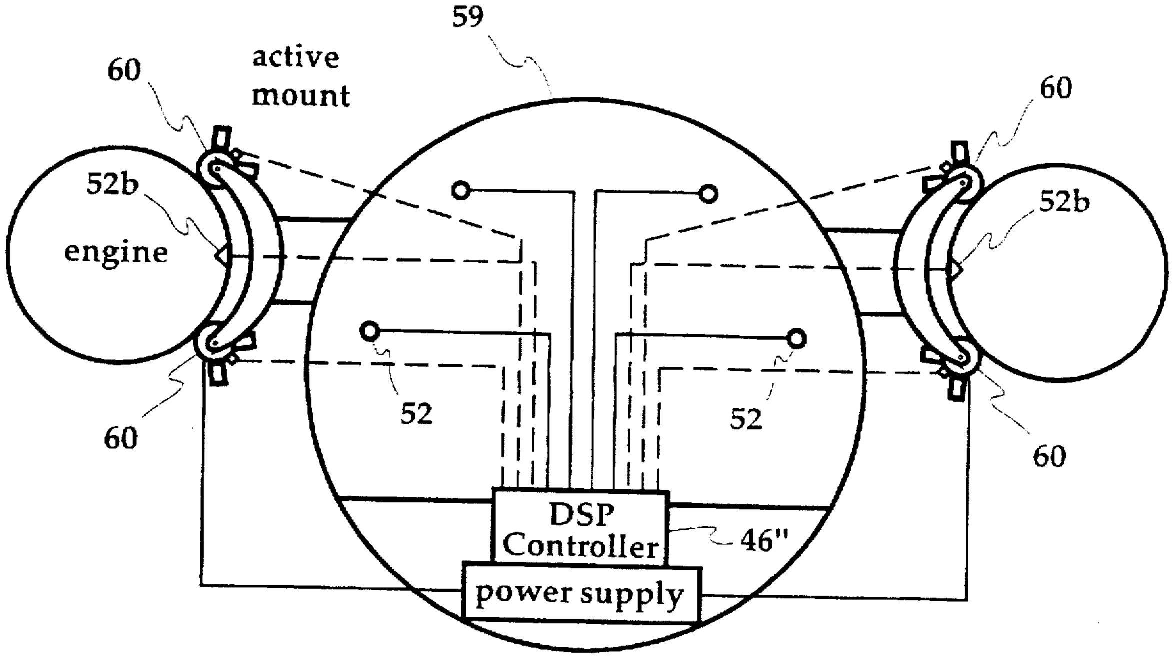
FIG. 17 is a schematic cross-sectional end view of a broadband control system employed in a turbofan aircraft which uses an active mount.

FIG. 17 depicts a broadband cancellation system 40" in conjunction with a turbofan aircraft 59. Engines 61 are mounted to the airframe using active mounts 60 in accordance with the more detailed description found in copending application Ser. No. 08/160,945 filed Jun. 16, 1994 entitled "Active Mounts for Aircraft Engines", which is hereby incorporated by reference. Inputs from microphones 52" and accelerometers 52b are fed to the controller 46" and are weighted and summed to produce a command signal which controls the actuators within active mounts 60. The combination of microphones 52" and accelerometers 52b enables the actuators within active mounts 60 to be manipulated to effectively control noise and vibration within compartment 41".

Various changes, alternatives and modifications will be apparent to one of ordinary skill in the art following a reading of the foregoing specification. It is intended that all such changes, alternatives and modifications as fall within the scope of the appended claims be considered part of the present invention.

We claim:

1. An active vibration control system for controlling vibrational energy within an enclosure such as an aircraft cabin, an automobile passenger compartment, and the like, said system being capable of a broadened control and comprising:

a) reference sensor means for monitoring a disturbance to be controlled, said disturbance having various spectral frequencies contained therein, said reference sensor means producing a reference signal which corresponds to said disturbance;

b) first frequency-focused structural actuator means for producing a low-frequency vibrational control signal reducing at least a first portion of said disturbance by interfering with some of said various spectral frequencies;

c) second frequency-focused acoustic actuator means within said enclosure for producing a higher-frequency acoustic control signal canceling at least a second portion of said disturbance by interfering with other of said various spectral frequencies;

d) an adaptive controller including adaptive filter means for processing said reference signal and producing at least two actuator command signals, one each to said first frequency-focused structural actuator means and said second frequency-focused acoustic actuator means, which are of appropriate frequency and magnitude to activate a respective said actuator means;

e) error sensor means for sensing a residual signal resulting from combining said low-frequency vibrational control signal and said higher-frequency acoustic control signals with said disturbance, and f) circuitry means for feeding said residual signal back to said adaptive filter means to make adjustments in said at least two actuator command signals.

2. The active vibration control system of claim 1 wherein said passenger compartment has K acoustic modes and said system further comprises M first frequency-focused structural actuator means where M≧K.

3. The active vibration control system of claim 2 wherein said system includes L error sensor means within said compartment and N second-frequency focused acoustic actuators, where N≧L/2.

4. The active vibration control system of claim 1 further comprising means to frequency focus said reference signal prior to feeding it to said adaptive controller.

5. The active vibration control system of claim 4 wherein said means to frequency focus said reference signal comprises a filter selected from the group consisting of a low pass filter, a high pass filter, and a band pass filter.

6. The active vibration control system of claim 1 wherein said first frequency-focused structural actuator means comprise at least one inertial shaker and said second frequency-focused acoustic actuator means comprise at least one speaker.

7. The active vibration control system of claim 1 wherein said error sensor means comprise one or more spaced microphones within said enclosure.

8. The active vibration control system of claim 1 wherein said error sensor means comprise one or more spaced frequency focused accelerometers attached to structural portions of said enclosure.

9. The active vibration control system of claim 1 wherein said enclosure is an aircraft cabin of a turboprop aircraft.

10. The active vibrational control system of claim 9 wherein said first frequency-focused structural actuator means is a counter-vibration producing element and is attached to said enclosure and is focused to a frequency corresponding to a primary blade passage frequency 4P and said second frequency-focused acoustic actuator means is a speaker and is focused to a frequency corresponding to a second or higher harmonic of said blade pass frequency.

11. The active vibration control system of claim 1 wherein said enclosure is a cabin of a helicopter.

12. The active vibration control system of claim 11 wherein said first frequency-focused structural actuator means comprises at least one structural actuator positioned beneath one or more seats within said cabin and said second frequency-focused acoustic actuator means comprises a plurality of speakers positioned in a vicinity of a passenger's head.

13. The active vibration control system of claim 12 wherein said plurality of speakers are mounted upon headrest means within said cabin.

14. The active vibration control system of claim 1 wherein said first frequency-focused structural actuator means interfere with some of said various spectral frequencies which are directly coupled to structural vibration of said enclosure and said second frequency-focused acoustic actuator means interfere with other of said various spectral frequencies which are uncoupled to said structural vibration of said enclosure.

15. An active control system for controlling vibrational energy within an enclosure such as an aircraft cabin, an automobile passenger compartment, and the like, said system comprising:

a) reference sensor means for monitoring a disturbance to be controlled , said disturbance having various spectral frequencies contained therein, said reference sensor means producing a reference signal which corresponds to said disturbance;

b) first frequency-focused structural actuator means for producing a first cancelling signal reducing at least a first portion of said disturbance by interfering with some of said various spectral frequencies which are directly coupled to structural vibration of said enclosure;

c) second frequency-focused acoustic actuator means for producing a second cancellation signal canceling at least a second portion of said disturbance by interfering with other of said various spectral frequencies which are uncoupled to structural vibration of said enclosure;

d) an adaptive controller including adaptive filter means for processing said reference signal and producing at least two actuator command signals, one each to said first frequency-focused structural actuator means and second frequency-focused acoustic actuator means, which are of appropriate frequency and magnitude to activate a respective said actuator means;

e) error sensor means for sensing a residual signal resulting from combining said first cancellation signal and said second cancellation signal with said disturbance, and f) circuitry means for feeding said residual signal back to said adaptive filter means to make adjustments in said at least two actuator command signals.

16. An active control system for controlling a disturbance generated by and aircraft engine various spectral frequencies including an N1 frequency range and a higher N2 frequency range emerging within an enclosure such as an aircraft cabin, said system comprising:

a) reference sensor means for monitoring said disturbance to be controlled and producing a reference signal which corresponds to said disturbance;

b) first frequency-focused structural actuator means for producing a first cancelling signal within said N1 frequency range reducing at least a first portion of said disturbance by interfering with some of said various spectral frequencies that are within said N1 frequency range;

c) second frequency-focused structural actuator means for producing a second cancelling signal within said N2 frequency range reducing at least a second portion of said disturbance by interfering with some of said various spectral frequencies that are within said N2 frequency range;

d) an adaptive controller including adaptive filter means for processing said reference signal and producing at least two actuator command signals, one each to said first frequency-focused structural actuator means and said second frequency-focused structural actuator means, which are of appropriate frequency and magnitude to activate a respective said actuator means;

e) error sensor means for sensing a residual signal resulting from combining said first cancellation signal, said second cancellation signal, and said disturbance, and f) circuitry means for feeding said residual signal back to said adaptive filter means to make adaptations in said at least two actuator command signals.

17. An active control system of claim 16 wherein said first frequency-focused structural actuator means is tuned to a low end of said N1 frequency range and said second frequency-focused structural actuator means is tuned to a low end of said N2 frequency range.

18. An active vibration control system for controlling vibrational energy within an enclosure such as an aircraft cabin, an automobile passenger compartment, and the like, said system being capable of a broadened control and comprising:

a) reference sensor means for monitoring a disturbance to be controlled, said disturbance having various spectral frequencies contained therein, said reference sensor means producing a reference signal which corresponds to said disturbance;

b) frequency-focused structural actuator means for producing a vibrational control signal within a first frequency range reducing at least a first portion of said disturbance by interfering with some of said various spectral frequencies;

c) frequency-focused acoustic actuator means within said enclosure for producing an acoustic control signal within a second frequency range canceling at least a second portion of said disturbance by interfering with other of said various spectral frequencies;

d) a controller including adaptive filter means for processing said reference signal and producing at least two actuator command signals, one each to said frequency-focused structural actuator means and said frequency-focused acoustic actuator means, which are of appropriate frequency and magnitude to activate a respective said actuator means;

e) error sensor means for sensing a residual signal resulting from combining said vibrational control signal and said acoustic control signals with said disturbance, and f) circuitry means for feeding said residual signal back to said adaptive filter means to make adjustments in said at least two actuator command signals.

* * * * *